(12) United States Patent
Orlowski et al.

(10) Patent No.: US 9,750,403 B2
(45) Date of Patent: Sep. 5, 2017

(54) RETINAL MOVEMENT TRACKING IN OPTICAL COHERENCE TOMOGRAPHY

(71) Applicant: CANON KABUSHIKI KAISHA, Tokyo (JP)

(72) Inventors: Slawomir Orlowski, Torun (PL); Tomasz Dziubak, Torun (PL); Jakub Szatkowski, Górsk (PL); Pawel Dalasinski, Torun (PL); Maciej Pańkowiec, Torun (PL)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/519,983

(22) Filed: Oct. 21, 2014

(65) Prior Publication Data

US 2015/0109579 A1   Apr. 23, 2015

(30) Foreign Application Priority Data

Oct. 23, 2013 (EP) .................................... 13189854

(51) Int. Cl.
*A61B 3/10* (2006.01)
*A61B 3/12* (2006.01)
*A61B 3/113* (2006.01)

(52) U.S. Cl.
CPC .............. *A61B 3/102* (2013.01); *A61B 3/10* (2013.01); *A61B 3/113* (2013.01); *A61B 3/1225* (2013.01); *A61B 3/1233* (2013.01)

(58) Field of Classification Search
CPC  A61B 3/10; A61B 3/102; A61B 3/113; A61B 3/1225; A61B 3/1233
USPC .......................................... 351/200, 205, 206
See application file for complete search history.

(56) References Cited

U.S. PATENT DOCUMENTS

| | | | | |
|---|---|---|---|---|
| 2008/0100612 A1* | 5/2008 | Dastmalchi | ............ | A61B 3/102 345/418 |
| 2008/0239240 A1* | 10/2008 | Tsukada | ................. | A61B 3/102 351/211 |
| 2010/0110172 A1* | 5/2010 | Satake | .................. | A61B 3/102 348/78 |

(Continued)

FOREIGN PATENT DOCUMENTS

| EP | 2420181 A1 | 2/2012 |
|---|---|---|
| EP | 2620096 A2 | 7/2013 |

*Primary Examiner* — William R Alexander
(74) *Attorney, Agent, or Firm* — Canon USA, INC. IP Division

(57) ABSTRACT

The present invention defines a method of correcting for eye movement during optical coherence tomography imaging. The method includes imaging (by scanning) a fundus of an eye to obtain a fundus image (for example, using an SLO); scanning the fundus to obtain a plurality of tomographic images (for example, using OCT); determining, at predetermined intervals, an alignment of the tomographic images with respect to the fundus image, and, if it is determined that there is a misalignment, determining the number of tomographic images that have been scanned in the predetermined interval since the previous alignment determination; determining the offset by which the tomographic images are misaligned; applying the offset to the next tomographic image to be scanned and rescanning the determined number of tomographic images that were scanned during the interval between misalignment being determined and offset being applied.

16 Claims, 9 Drawing Sheets

(56) References Cited

U.S. PATENT DOCUMENTS

| | | | | |
|---|---|---|---|---|
| 2011/0199579 | A1* | 8/2011 | Muto | A61B 3/14 |
| | | | | 351/208 |
| 2011/0267580 | A1* | 11/2011 | Nakajima | G06K 9/00597 |
| | | | | 351/206 |
| 2012/0033181 | A1* | 2/2012 | Koizumi | A61B 3/102 |
| | | | | 351/208 |
| 2012/0229764 | A1* | 9/2012 | Tomatsu | A61B 3/113 |
| | | | | 351/206 |
| 2012/0229765 | A1* | 9/2012 | Makihira | A61B 3/102 |
| | | | | 351/206 |
| 2012/0249956 | A1* | 10/2012 | Narasimha-Iyer | A61B 3/102 |
| | | | | 351/206 |
| 2012/0249961 | A1* | 10/2012 | Muto | A61B 3/152 |
| | | | | 351/208 |
| 2013/0093995 | A1* | 4/2013 | Suehira | A61B 3/102 |
| | | | | 351/206 |
| 2013/0107213 | A1* | 5/2013 | Muto | A61B 3/102 |
| | | | | 351/208 |
| 2013/0176532 | A1 | 7/2013 | Sharma et al. | |
| 2013/0195336 | A1* | 8/2013 | Uchida | A61B 3/102 |
| | | | | 382/131 |

* cited by examiner

RETINAL MOVEMENT TRACKING IN OPTICAL COHERENCE TOMOGRAPHY

This application claims the benefit under 35 U.S.C. §119 (a)-(d) of United Kingdom Patent Application No. 13189854.6, filed on Oct. 23, 2013 and entitled "RETINAL MOVEMENT TRACKING IN OPTICAL COHERENCE TOMOGRAPHY." The above cited patent application is incorporated herein by reference in its entirety.

TECHNICAL FIELD

The present invention relates to the imaging of a fundus oculi using in particular optical coherence tomography (OCT). More specifically, the present invention relates to the correction of OCT images when the fundus oculi moves during imaging.

BACKGROUND ART

Optical coherence tomography (OCT), though used in many medical and biological fields for medical imaging, is particularly suited to ophthalmic imaging because it is non-invasive and can be performed even through the anterior structures of the eye to obtain a 3-D image of the fundus oculi (i.e. the retina of the eye).

Various ophthalmic apparatuses that use optical apparatuses are known in the art, such as an anterior ocular segment imaging apparatus that images the anterior portion of the eye; a fundus camera that takes an image of the fundus of the eye; a scanning laser ophthalmoscope (SLO) for taking an image of the fundus, and so on. Ophthalmic use of OCT is also well-known and described in the art, such as in US2012/0033181 (KK Topcon) and in D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, "Optical Coherence Tomography", Science 254, 1178-1181 (1991).

Partial coherence interferometry for use in ophthalmology is discussed in A. F. Fercher, C. K. Hitzenberger, G. Kamp, S. Y. El-Zaiat "Measurements of intraocular distances by backscattering spectral interferometry," Opt. Comm. 117, 43-48 (1995).

Ophthalmic use of spectral OCT is described in M. Wojtkowski, A. Kowalczyk, R. Leitgeb, and A. F. Fercher, "Full range complex spectral optical coherence tomography", Opt. Lett. 27, 1415-1418 (2002).

OCT is particularly useful because it can obtain tomographic images in the depth direction of the fundus (for example, to obtain a 3-dimensional image of the fundus structure) whereas other imaging apparatuses image only the surface of the fundus. OCT uses low-coherent light with multiple wavelengths as a measurement beam to irradiate the fundus of the eye to be examined. The various wavelengths penetrate into the fundus by a different amount before reflecting back into the OCT's optical system. This reflected beam interferes with a reference beam that corresponds to the measurement beam and the resultant interference beam is detected to build up a tomographic image in a depth-direction. The greater the wavelength bandwidth, the greater the resolution of the resultant tomographic image because different wavelengths penetrate the fundus to different depths and reflect differently from the fundus.

Each depth-direction scan is referred to as an "a-scan". A plurality of a-scans in a single scan line (defined by the scanning direction of the OCT apparatus) is referred to as a "b-scan". A plurality of b-scans may be combined to build up a 3-D image. A "tomographic image" is a cross-sectional image of the fundus oculi and may follow a b-scan line or it may be perpendicular to the b-scan direction or it may be at any angle in between when it is generated by the interpolation of the 3-D volume of the fundus oculi using the OCT b-scans. In the present discussion, using Cartesian coordinates, the b-scans extend in the x-direction, the thickness of the fundus is in the z-direction and the y-direction is in the fundus plane but perpendicular to the b-scanning direction.

In order to provide enough information to enable a confident diagnosis of eye health, OCT manufacturers have combined OCT (for depth-direction tomographic imaging) with fundus imaging (for fundus observation) and sometimes anterior eye imaging (for anterior eye observation). These may even be combined in the same device.

Advantage of including anterior eye images is that such an image may be used to align the optical paths of other imaging devices with the iris of the eye. Further to this, anterior eye disease such as cataracts or other opaque portions on the lens or iris that may cause shadows on the fundus can be seen and the OCT measurement beam can be directed to a position on the lens or iris of the eye other than those positions with opaque portions.

An advantage of including a fundus image is that it can help with alignment of tomographic images. A mark superimposed on a fundus image may indicate the position of a tomographic image, the tomographic image being perpendicular to the plane of the fundus image. A fundus image may even be marked by an ophthalmologist to indicate where on the fundus they would like a tomographic image to be scanned or to indicate which fundus cross-section they would like to view.

Taking a fundus image has a further advantage of helping to align tomographic images both with the fundus so that an ophthalmologist knows where on the fundus a particular tomographic image has been taken and also with each other so that a 3-D image may be correctly assembled from a plurality of tomographic images. Furthermore, a fundus image may be used to ensure that a-scans within a b-scan are aligned to help to ensure a consistent b-scan.

The reason that alignment is a concern is that during scanning by an OCT apparatus, a person's eye is prone to movement. This movement may be blinking or saccades or some other form of voluntary or involuntary movement.

There are different ways in which eye movement is corrected or compensated for. One type of correction involves tracking the movement of the eye using a fundus image as a tracking image, for instance, and adjusting the position of the OCT measurement beam in real time to maintain the same location of an OCT scan with respect to the tracking image. This is seen in commercially-available OCT apparatuses such as Canon's OCT HS100, Nidek's RS-3000, Topcon's OCT-2000, Heidelberg's Spectralis and Carl Zeiss Meditec's Cirrus HD-OCT.

In Topcon's OCT-2000 (see also US 2012/0033181 A1), the positions of the OCT b-scans 2000 are observed relative to fundus images 1000 as can be seen in FIGS. 3A, 3B and 3C. Although the images are shown as b-scans 2000 moving with respect to the fundus images, it is in fact the fundus that is moving and the b-scans are scanning in a constant position as defined in 3-D space. The fundus image acquisition is so much faster than the OCT scans over the same area that the fundus image is much more likely to be in alignment with the fundus and its position is therefore regarded to be the same as the fundus position. The fundus moves between (or even during) b-scans to cause the relative movement artifacts. However, this relative movement is more easily depicted in the figures as b-scan misalignments with the fundus image being constant.

FIG. 3A shows an ideal scan with no misalignments as imaged by Topcon's OCT-2000. The fundus image 1000 is aligned with b-scans 2000, which are themselves equally spaced apart in the y-direction and are all straight and aligned with each other, representing alignment in the x-direction. In Topcon's OCT-2000, the b-scans 2000 contain extra a-scans 300 at each end so that when misalignment occurs in the x-direction within a certain threshold, as shown by b-scans 302 and 312 in FIG. 3B, during post-processing off-line, those b-scans can be adjusted so that only the a-scans that are in line with the fundus image 1000 are used. However, if a b-scan is misaligned by more than the threshold, such as b-scan 308 in FIG. 3B, this b-scan needs to be re-scanned.

One problem with this known apparatus is that much more information has to be processed than necessary because every single b-scan has more a-scans than will be used to form a tomographic image. This causes an extra processing burden and slows down processing.

FIG. 3C shows the known system with alignment corrected in the x-axis but not in the y-axis. Y-axis compensation is performed by comparing the obtained b-scans with the fundus image and determining where scan lines are densely packed, such as lines 304 and 306, and where scan lines are too far apart, such as between lines 318 and 320. Densely packed lines can be thinned if necessary and thinly packed lines can be interpolated to create scan lines where they are missing. If lines are separated by a distance greater than a threshold, they are re-scanned.

Another problem with some known apparatuses is that synchronisation between the fundus image and the b-scan of the OCT has to be constantly monitored, and this increases processing burden as well as increasing the time taken to create a tomographic image if no scanning is performed during the synchronisation process or if b-scans have to be corrected if an asynchronicity is found.

Specifically, there is a trade-off between a fundus image frame rate and an OCT b-scan rate. OCT b-scans are synchronised with fundus images. As a full fundus image (1000 in FIG. 3A) is scanned at a rate that is much faster than an OCT image (400 in FIG. 3A), one fundus image can be scanned in the time it takes to scan a number of a-scans within an OCT b-scan. As each fundus image is synchronised with the OCT image and this synchronisation takes time, if the fundus image capture rate increases, the number of times that synchronicity is checked per OCT image increases and the rate of capture of an OCT image necessarily decreases.

Heidelberg's Spectralis apparatus simultaneously images the fundus oculi with two beams of light. A first beam captures a fundus image to track eye movement. Using this image as a reference, the second beam is directed to the desired location on the fundus. This dual-beam technology mitigates eye motion artifacts, preventing them in the first place. During the measurement phase, this apparatus determines whether the eye is focused on a fixation target. The capture of the OCT b-scans is performed only if the eye is so focused. If not, the OCT system waits for the focus of the eye on the fixation target. Although this reduces the number of artifacts in the obtained OCT image, the measurement and image-capturing time is significantly extended.

Any kind of fundus tracking has a problem of a "feedback" delay in the feedback loop that occurs between the fundus tracking and the OCT correcting for misalignments found during the tracking. Several b-scans may be completed in the time it takes for the measurement system to determine that a misalignment between the fundus image and the OCT b-scan has occurred. Thus, several misaligned b-scan images may be taken before the misalignment is noticed. Measurement of the alignment of all of those b-scans may then be required to compensate for their misalignment.

SUMMARY OF THE INVENTION

In consideration of the above problems, it is desired to provide an OCT apparatus that provides a high-quality, high scan-rate fundus image suitable for observation (or "preview") without sacrificing OCT scan rate in the correction of eye movement artifacts in tomographic images. It is also desired to reduce the effects of feedback loops caused by alignment measurements being performed after acquisition of OCT scan data.

According to a first aspect of the present invention, there is provided a method of correcting for eye movement during optical coherence tomography imaging, the method including imaging a fundus of an eye to obtain a fundus image, imaging the fundus to obtain a plurality of tomographic images. The method also includes determining, during the imaging of the fundus to obtain the plurality of tomographic images, an alignment of the tomographic images with respect to the fundus, and, if it is determined that there is a misalignment. The method continues with determining the number of tomographic images that have been imaged in an interval since the misalignment determination, and re-imaging the determined number of tomographic images.

BRIEF DESCRIPTION OF THE DRAWINGS

The invention will be described below purely by way of example with reference to the following figures.

DESCRIPTION OF THE EMBODIMENTS

Figure 1:
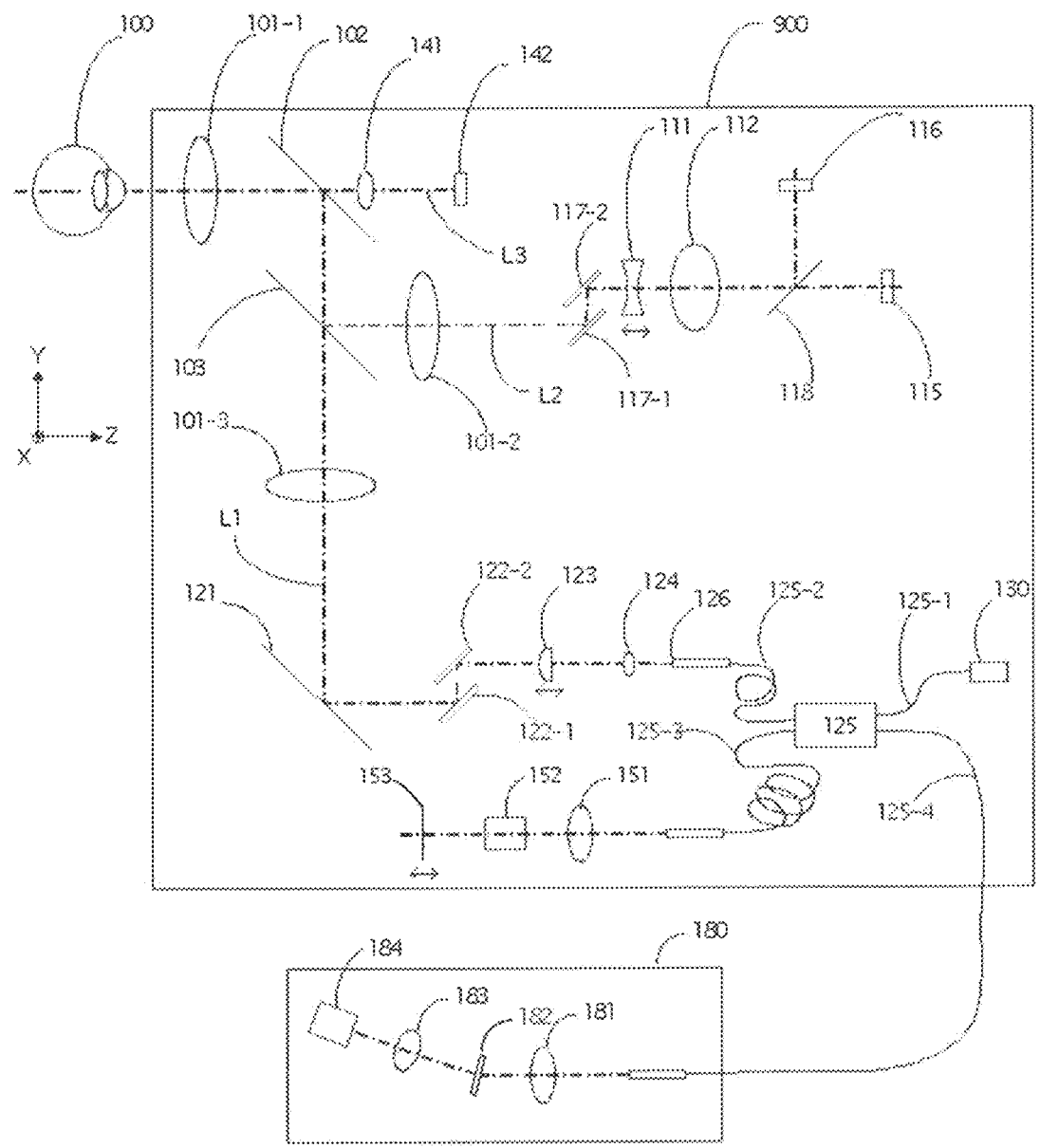
FIG. 1 is a schematic diagram of an optical coherence tomographic apparatus with scanning laser ophthalmoscope according to a preferred embodiment.

The arrangement of an optical coherence tomographic apparatus (OCT apparatus) will be described with reference to FIG. 1. The optical coherence tomographic apparatus includes an optical head 900 and a spectrometer 180. The optical coherence tomographic apparatus obtains a tomographic image of an object to be examined based on the light obtained by combining return (i.e. reflected, but also some scattered) light from the object that has been irradiated with measurement light with reference light corresponding to the measurement light.

The internal arrangement of the optical head 900 will be described first. The optical head 900 comprises a measurement optical system for capturing an anterior eye image of an eye 100 to be examined as well as a two-dimensional image and a tomographic image of the fundus. An objective lens 101-1 is disposed to face the eye 100. On the optical axis of this lens, a first dichroic mirror 102 and a second dichroic mirror 103 serve as optical path branching units. The two dichroic mirrors 102 and 103 split the optical path for each wavelength band into a measurement optical path L1 of an OCT optical system, a fundus observation/fixation lamp optical path L2, and an anterior ocular segment observation optical path L3.

A lens 141 and an infrared CCD 142 for anterior eye observation are disposed on the optical path L3. The infrared CCD 142 has sensitivity near the wavelength of anterior eye observation illumination light (not shown), more specifically, 970 nm.

Optical path L2 will now be described. There are three lenses 101-2, 111 and 112 and lens 111 is driven by a motor (not shown) for focus adjustment for a fixation lamp and for fundus observation. A light source 115 generates light having a wavelength of 780 nm. An X scanner 117-1 and a Y scanner 117-2, which serve to scan the light emitted from the light source 115 for fundus observation on the fundus of the eye 100, are also disposed on the optical path L2. The lens 101-2 is disposed such that its focal position is located near a central position between the X scanner 117-1 and the Y scanner 117-2. The X scanner 117-1 is formed from a polygon mirror to scan in the X direction at high speed. The X scanner 117-1 may be formed from a resonance mirror. A single detector 116 is formed from an APD (avalanche photodiode), and detects light scattered/reflected by the fundus. A prism 118 is a prism on which a perforated mirror or hollow mirror is deposited, and it separates illumination light emitted by a light source 115 from return light from the fundus.

The optical path L1 is that of an OCT optical system and is used to capture a tomographic image of the fundus of the eye 100. This optical path is used to obtain interference light for forming a tomographic image. A lens 101-3, a mirror 121, an X scanner 122-1 and a Y scanner 122-2 are disposed on the optical path L1. The X scanner 122-1 and Y scanner 122-2 scan light onto the fundus of the eye 100 in the X direction (main scanning direction or b-scan direction) and the Y direction (sub-scanning direction) intersecting the first direction. The optical path between the X scanner 122-1 and the Y scanner 122-2 in FIG. 1 is illustrated as running in a direction parallel to the drawing surface. In practice, however, this optical path runs in a direction perpendicular to the drawing surface.

A light source 126 provides measurement light to a measurement optical path. The measurement light source 126 is disposed on a fibre end and is optically conjugate to the fundus region of the eye 100. On the same optical path are lenses 123 and 124 and lens 123 is driven by a motor (not shown) in the directions indicated by a double-headed arrow to perform focus adjustment. The focus adjustment lens 123 is disposed between the measurement light source 126 and the X scanner 122-1 and Y scanner 122-2, making it possible to use a lens no larger than the lens 101-3 or to not have to move a fibre 125-2 connected to the measurement light source 126.

This focus adjustment makes it possible to form an image of the measurement light source 126 on the fundus of the eye 100 and to transmit return light efficiently from the fundus of the eye 100 to the fibre 125-2.

The arrangements of the optical path of light emitted from a light source 130, a reference optical system and a spectrometer 180 in FIG. 1 will be described next. The light source 130, a mirror 153, a dispersion-compensating glass 152, an optical coupler 125, optical fibres 125-1 to 125-4, a lens 151, and the spectrometer 180 constitute a Michelson interferometer system. Any interferometer such as a Mach-Zehnder interferometer is also suitable. The optical fibres 125-1 to 125-4 are single-mode optical fibres, which are connected to the optical coupler 125 so as to be integrated.

The light emitted from the light source 130 is split into measurement light—which is transmitted to the optical fibre 125-2 through the optical fibre 125-1 and the optical coupler 125—and reference light which is transmitted to the optical fibre 125-3. The measurement light enters the fundus of the eye 100 through the above OCT optical system optical path and reaches the optical coupler 125 through the same optical path by reflection and scattering by the fundus.

Reference light is reflected by the mirror 153 and is transmitted through the optical fibre 125-3, the lens 151, and the dispersion-compensating glass 152 inserted to match the dispersion of the reference light with that of the measurement light. This light then returns along the same optical path and reaches the optical coupler 125.

The optical coupler 125 combines measurement light and reference light to form interference light. In this case, interference occurs when the optical path length of the measurement light is almost equal to that of the reference light. A motor and driving mechanism (not shown) adjust the position of the mirror 153 in the optical axis direction, thereby matching the optical path length of measurement light, which changes depending on the eye 100. Interference light is guided to the spectrometer 180 through the optical fibre 125-4.

The spectrometer 180 includes lenses 181 and 183, a diffraction grating 182 and a line sensor 184. The interference light emerging from the optical fibre 125-4 is made almost parallel through the lens 181, and then undergoes spectroscopic analysis by the diffraction grating 182 and image sensor.

Figure 2:
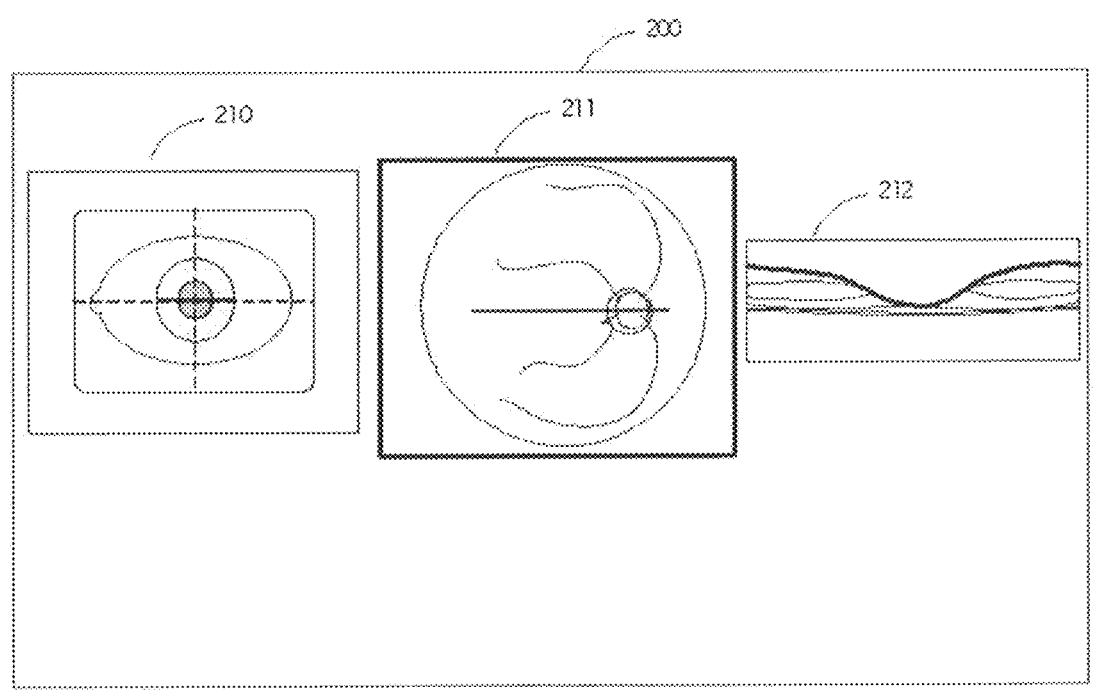
FIG. 2 is an example of a screen display including a tomographic image, fundus observation image and anterior ocular image.
Figure 3:
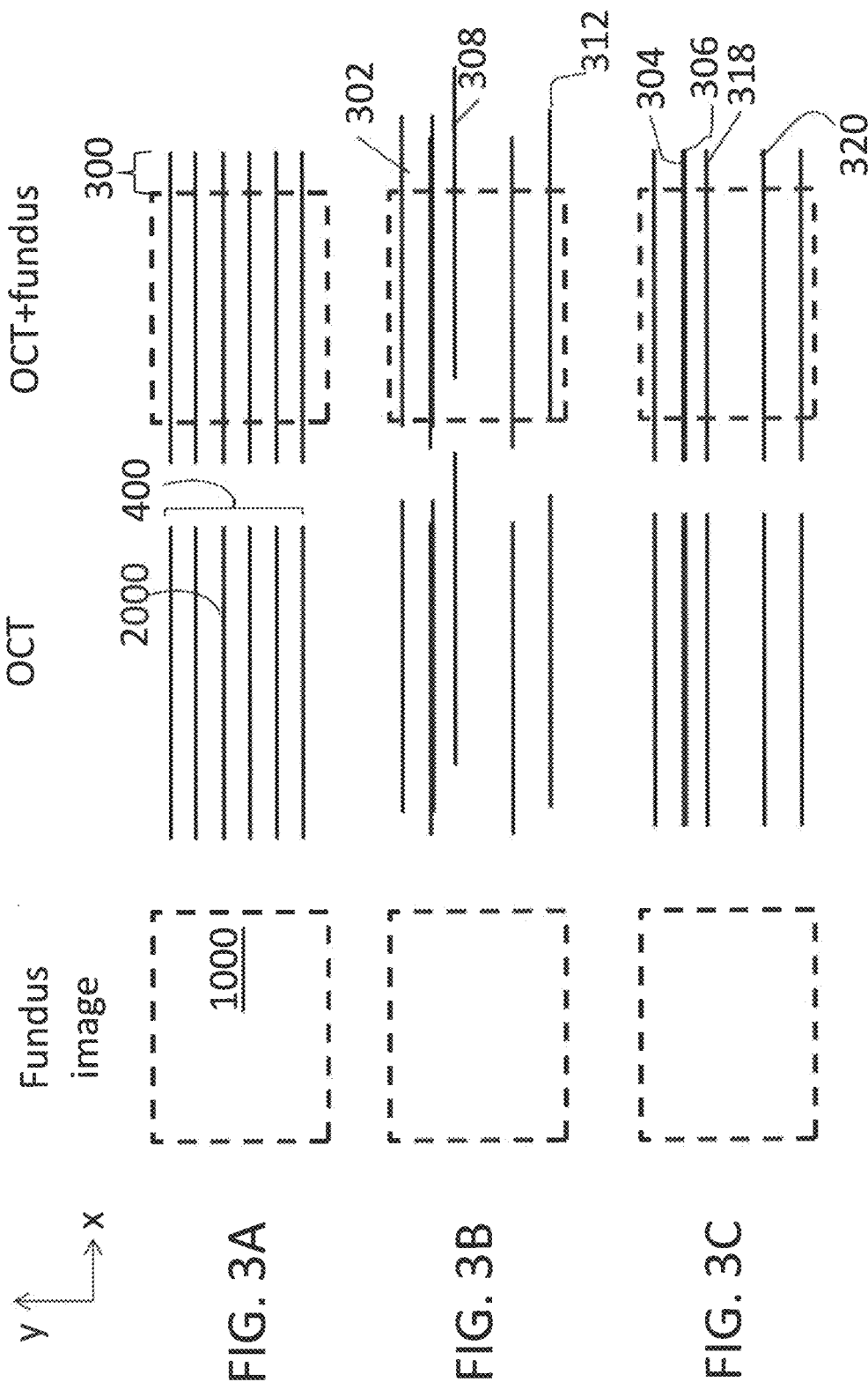
FIGS. 3A, 3B and 3C show a correction of alignment between SLO images and OCT images when eye movement occurs according to a known solution.

FIG. 2 shows an example of an anterior eye image 210, two-dimensional fundus image 211, and b-scan image 212 as a tomographic image displayed on a monitor 200. The anterior eye image 210 is the image which is output from the infrared CCD 142, processed, and displayed. The two-dimensional fundus image 211 is the image which is output from the CCD 116, processed, and displayed. The b-scan image 212 is the image which is output from the line sensor 184 and which is formed by the above processing.

As can be understood from the description above, the acquisition of tomographic images and the acquisition of fundus observation images are independent processes performed using independent light sources, sensors and optical paths. They can be the in the same or different apparatuses. However, they are most useful if they are mutually comparable by a processing apparatus and an ophthalmologist.

Although the present embodiment preferably includes the comparison of tomographic b-scan images with a 2-D fundus image such as that obtained using an SLO, other embodiments can be envisaged that determine tomographic image misalignment in other ways. The fundus image may be a projection image built up by coarse OCT scanning, for instance, or it may be taken with a fundus camera.

Generally, the way that eye movement is determined is by taking, imaging or building up two such fundus images sequentially and comparing them. A difference in position between the two images gives an alignment offset value. This difference in position may be divided with the time difference between the two images to obtain an eye movement velocity vector, giving a likely offset value for a subsequent image, too.

In order to be able to compare the position of two separate images with respect to an object on the fundus that is being imaged, it is valuable to synchronise the acquisition of the two images. The preferred fundus observation image forming device is an SLO for the purposes of the present embodiment and so the image forming device will be referred to hereinafter as an "SLO device".

An SLO device may scan a fundus image of a fundus region with 600 pixels in the y-axis and 800 pixels in the x-axis. It may produce images at a rate of 15 images per second (or frames per second: fps) and if the images are two interlaced images, the SLO device is in fact producing images at a rate of 30 fps. One image is represented as dotted square 1100 in FIG. 4.

Figure 4:
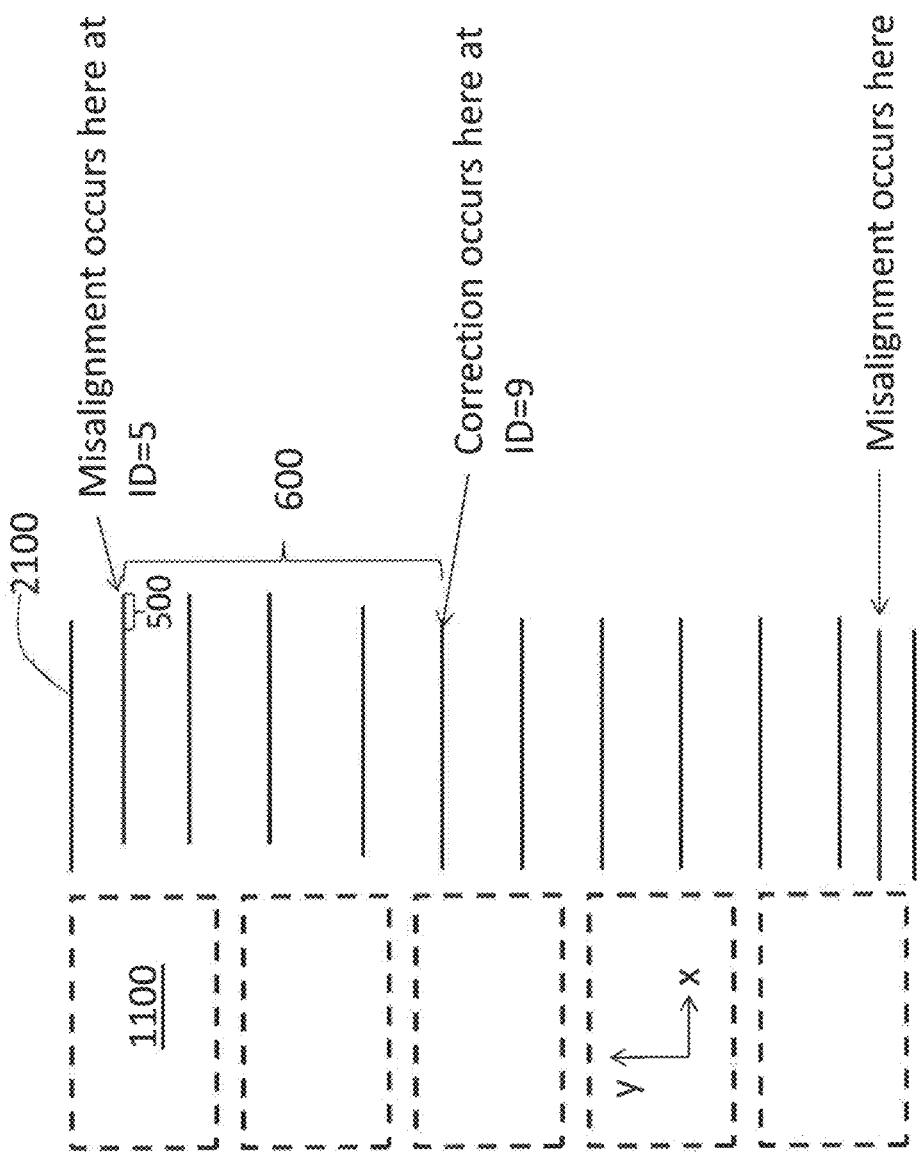
FIG. 4 shows a relationship between SLO images and OCT images when eye movement occurs.

On the other hand, a single OCT b-scan, shown as line 2100 in FIG. 4, comprises 1024 (or 512) a-scans and is scanned at a rate of 64 fps. In a region covered by 600 SLO lines, there are 128 OCT b-scan lines, and for the time taken to scan one SLO image (or two interlaced images), two OCT b-scan lines can be scanned.

If alignment were to be checked every time a new SLO image was taken, this would occur approximately every 2000 a-scans, or just under every two b-scan lines. Alignment checks take a finite amount of time and the next a-scan might not be scanned until the alignment check was complete. Thus, performing alignment checks in this way reduces OCT scan rate.

According to a preferred embodiment of the present invention, therefore, in order to overcome this trade-off between fundus observation image scanning rate and OCT scanning rate, a single-point synchronisation process of both modalities is performed. This is known as a "common start" or "synchronised start". According to this process, the acquisition of an image by the SLO and by the OCT are synchronised in time. A fundus observation image and an OCT b-scan are thereby started at the same time. After the start of both scanning acquisitions, both devices work independently. This way, a highest b-scan rate and fundus imaging rate (limited by hardware) is obtainable. Because the acquisition period of fundus observation images and OCT b-scans are well defined in time, it is possible to correlate fundus frames with OCT b-scans without the need for additional, physical synchronisation of both modalities. It is noted that although the same area is scanned by the SLO at the start of each synchronised start process, a different start position corresponding to a current b-scan of the OCT device will be synchronised with the SLO image. Nevertheless, the b-scans will all be within the same region as the SLO fundus image with which they are synchronised. This will be described in more detail below.

According to an embodiment of the present invention, the next step is that, for each image of the SLO fundus observation imaging process, a tracking algorithm determines the movement of the fundus by correlating a portion of the image with a reference image (which can simply be the most recent image already taken). Details of such a tracking algorithm are known in the art such as in Japanese application number JP2012-190617. The tracking algorithm outputs coordinates in x-y axes corresponding to movements of the fundus, these coordinates being known as offsets, and a flag which gives information regarding whether the tracking algorithm was able to track the fundus movement, the flag being a "fail" flag in the case where the tracking algorithm was not able to track the fundus movement. In the case of an eye blink or a very large eye movement, the tracking algorithm cannot determine the x-y offsets of the fundus movement and it sets the fail flag.

After the common start of the SLO fundus image scanning and the OCT b-scan scanning, a set of b-scans is collected within a predetermined time interval known as a first examination period.

During the first examination period, the offset 500 in the x-axis and the offset 502 in the y-axis are determined by the tracking algorithm and are provided to an OCT light beam control unit, which controls and thereby corrects—the position of the OCT scanning beam. These x-y offsets are provided to the OCT beam control unit at the time of scanning of each fundus observation image 1100. Ideally, the OCT beam control unit would take into account the newly-received x-y offsets for every b-scan 2100. As described above, a plurality (e.g. two) of the b-scans are collected during each single fundus observation image. Thus, the x-y offsets are generally newly determined every second b-scan.

To ensure that the b-scans are correctly correlated with their corresponding x-y offsets, the OCT beam control unit informs a system processing apparatus (e.g. Personal Computer) of an index number (ID) of the b-scan to which the offsets are to be applied. A list of such ID numbers is referred to as a feedback list. The feedback list, together with the x-y offsets, are collected by the system processing apparatus during the first examination period. This feedback list may be based on the number of b-scans completed since the previous "common start", as this is the most recent time that the SLO fundus image and the OCT b-scan are known to have been synchronized. Alternatively, the feedback list may be based on the number of b-scans completed since an offset was found, if this is different from the "common start" point.

Once the first examination period is finished, the system processing apparatus analyses the x-y offsets obtained during that first examination period. The acquisition of fundus observation images is precise (for example because of the SLO system being controlled by an FPGA (field-programmable gate array) driver unit) and the acquisition of OCT images is also accurate as a result of precise scanning and measurement techniques such as the use of a CCD (charge coupled device) linescan camera with well-controlled exposure time and line rate which is controlled by microprocessor unit. Thus, each b-scan can be assigned to a corresponding fundus observation image and thence to a corresponding set of offsets by means of the x-y offset list (generated by the tracking algorithm) and the feedback list (generated by the OCT's microprocessor unit).

In fact, what is determined from the x-y offset list and the feedback list is the difference between the b-scan that was misaligned (e.g. ID=5) and the b-scan to which the x-y offset was actually assigned (e.g. ID=9) after a feedback delay 600.

For example, for a given x-y offset 500, the system processing apparatus assigns the b-scan ID (e.g. ID=5) by taking into account known acquisition periods for both imaging modalities and knowing a common point in time such as the common start time. In a next step, the given x-y offset is searched for on the feedback list. From the feedback list, the current x-y offset is found to have been assigned to another b-scan ID (e.g. ID=9). The difference 600 between b-scan IDs (e.g. ID=5 to ID=9) is caused by the feedback loop of the b-scan correction system as mentioned above. Thus, the system processing apparatus can easily determine the b-scan range affected by the determined eye movement. This b-scan range is then communicated to the OCT apparatus and the affected b-scans are re-scanned or re-imaged.

Once the affected b-scan range is determined, the system processing apparatus performs a second examination repeats the acquisition of a list of affected b-scans. A similar analysis is applied to the second examination. In this way, the system processing apparatus can repeat examinations several times to enable the re-scan of all affected b-scans.

Depending on whether the re-scanning of the affected b-scans occurs at the end of a full OCT image or immediately after the offset is calculated and assigned to a set of b-scans, the second examination may be performed on a set of b-scans following the affected set (before re-scanning) or it may start again on the set of b-scans that have just been re-scanned.

Figure 5:
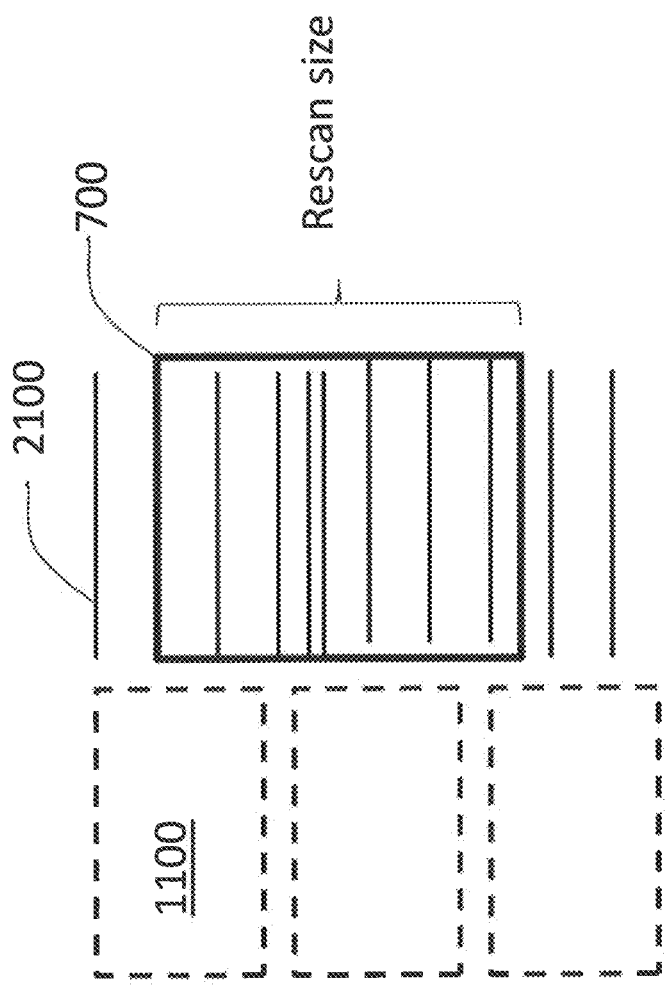
FIG. 5 shows a correction of alignment between SLO images and OCT images according to a preferred embodiment of the present invention.
Figure 6:
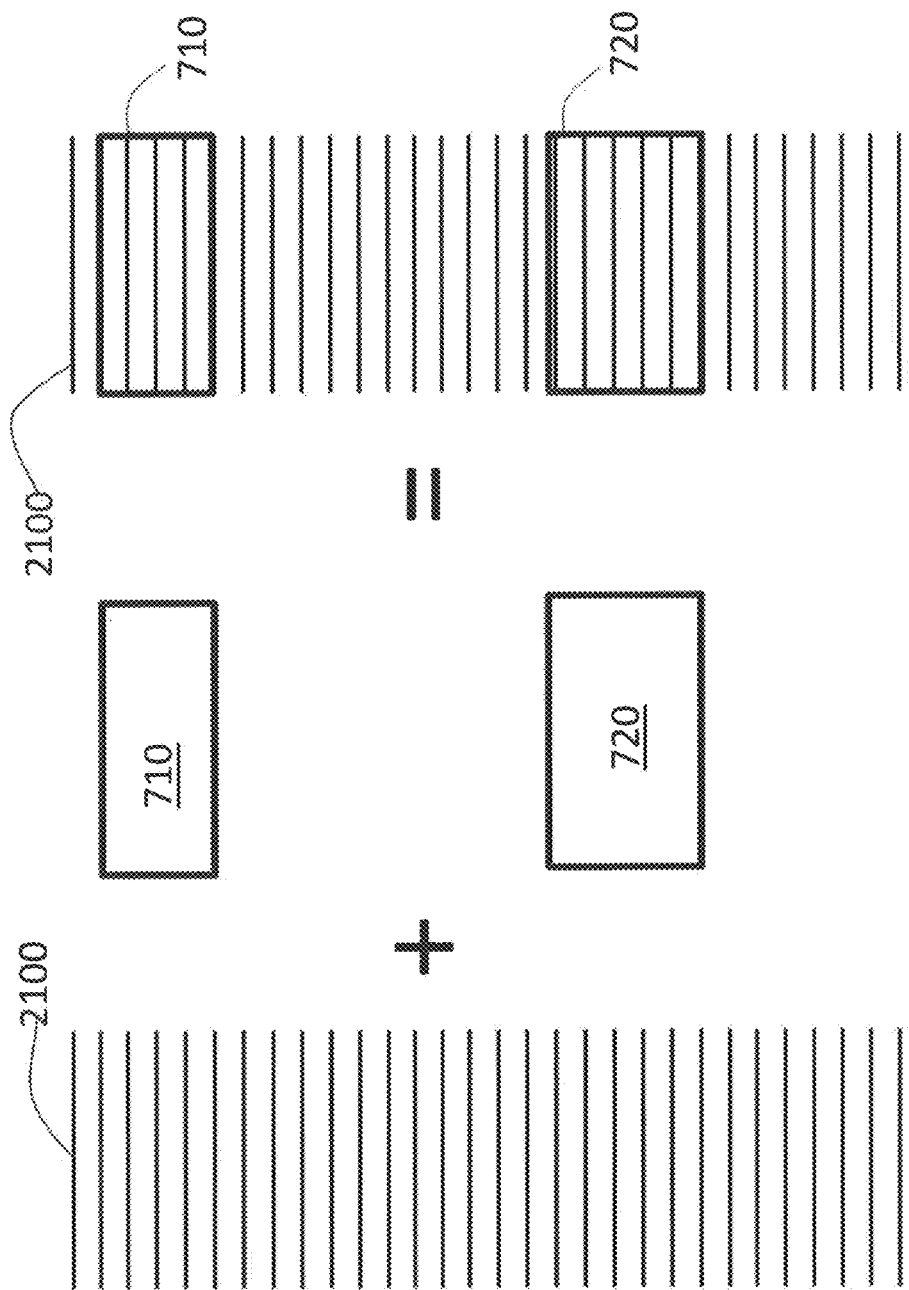
FIG. 6 shows a correction of alignment between SLO images and OCT images according to a preferred embodiment of the present invention.

FIG. 5 shows the fundus observation images 1100 and the OCT b-scans 2100. The affected b-scans that are to be re-scanned are boxed and labelled 700. FIG. 6 shows the final product from the OCT apparatus, namely the original b-scan images 2100 having had affected b-scans replaced by re-scans 710 and 720.

Figure 7:
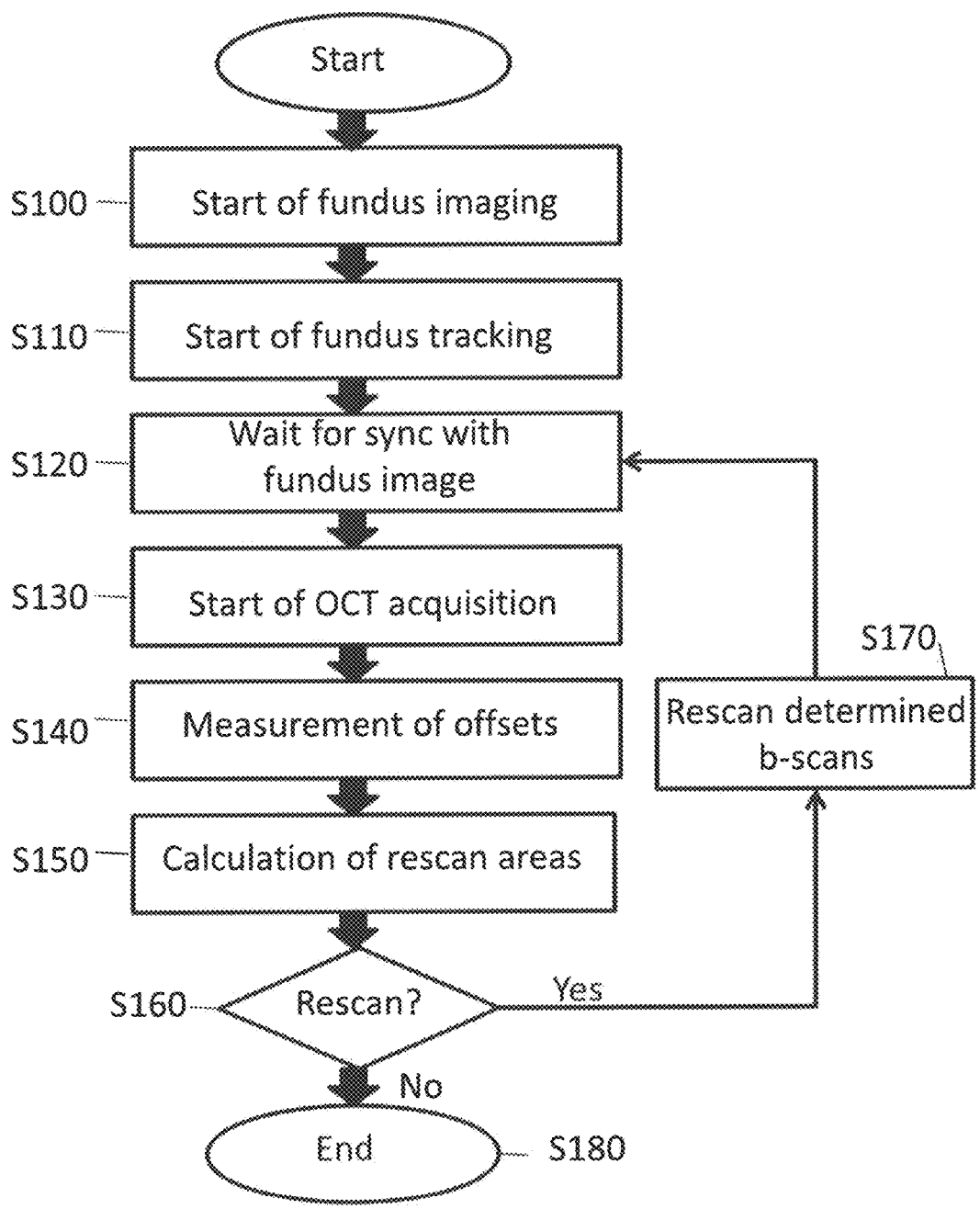
FIG. 7 is a flowchart showing a correction method according to a preferred embodiment of the present invention.
Figure 8:
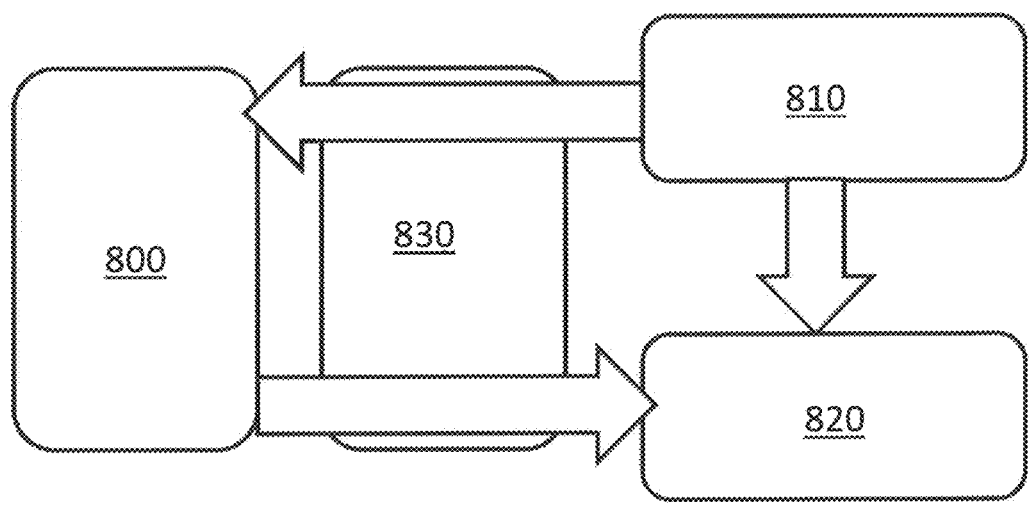
FIG. 8 shows a relationship between modules in a system for correcting for eye movement during OCT scanning according to an embodiment of the present invention.

FIG. 7 shows a flowchart of the process. FIG. 8 shows the various modules that are involved in performing the described process.

At step S100, the fundus observation by, for example, the SLO apparatus begins.

At step S110, the tracking algorithm is performed by the fundus tracking module 810 to find offsets in the x-y plane (the retina plane) using the SLO apparatus. The tracking mechanism traces voluntary and involuntary eye movement. It captures a reference image from the SLO modality and correlates scanned images with the reference image to determine the misalignment value. Based on this misalignment value, the tracking mechanism calculates an offset vector and passes this vector via a USB 830 to the OCT beam control unit 800. The OCT beam control unit 800 corrects offsets of OCT X- and Y-scanners 122-1 and 122-2 to align the OCT beam with the tracked fundus image orientation.

At step S120, the OCT beam control unit 800 waits for a fundus observation frame to begin being scanned. This is so that the "common start" process can occur to correlate the OCT b-scans with the SLO fundus images. The OCT beam control unit 800 can assign a specific b-scan to a specific SLO image or it can simply wait for the next fundus image to begin. At step S130, the OCT beam control unit begins its scanning process.

At step S140, the collection of the offsets begins using the tracking algorithm. In the preferred embodiment, the offsets are collected during measurement of the SLO image. These offsets define differences between the reference image and the current image being scanned by the SLO apparatus. These offsets are used by the OCT apparatus in real time during the capture of the OCT images by causing real-time movement of the OCT beam according to the offsets. However, as mentioned above, the movement of the OCT beam is not quite in real time, but has a delay caused by the amount of time it takes to calculate the offsets, to communicate between the fundus tracking module and the OCT scanning system and to reconfigure the OCT beam. This delay introduces a displacement on a fundus reconstruction image by the OCT apparatus as shown on FIG. 9.

Figure 9:
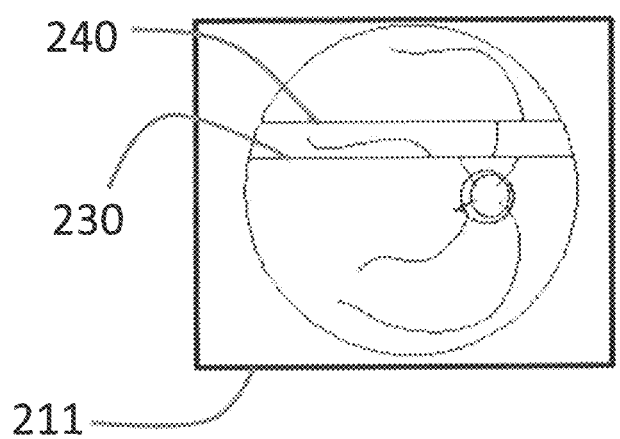
FIGS. 9 and 10 show how a misalignment caused by eye movement may appear on a display of the fundus oculi.
Figure 10:
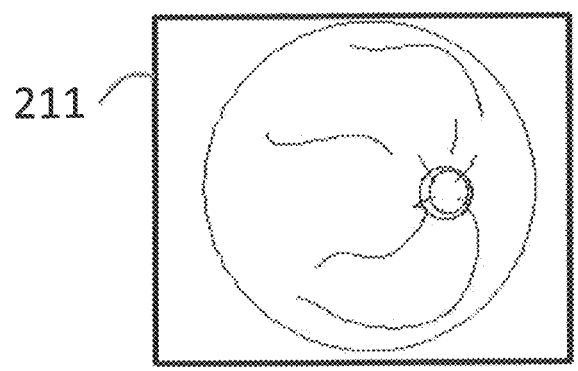

FIG. 9 shows the fundus image 210 of FIG. 2, but with displacement at lines 230 and 240. The lines are to demonstrate where the displacement is, but these would not necessarily appear on the display 200. FIG. 10 illustrates how the fundus image 210 would appear on the display 200, with the two displacements.

The OCT apparatus performs fundus reconstruction using the OCT scans captured during measurement with a raster protocol. In the case of a loss of tracking for a relatively considerable amount of time, such as in the case of a blink, there would be more than just a displacement shown in FIG. 9; there would be several "blank" b-scans resulting in a break in the OCT image. If the tracking module fails to track movement, it cannot calculate offsets and transmit these to the OCT beam control unit 800. Thus, the OCT beam control unit does not apply the offsets to the X-Y scanners and b-scans are not corrected. The b-scans that occurred while the tracking module failed to track movement of the eye are also re-scanned because it is not determinable whether the b-scans were aligned or not and so no correction can be applied as in the case when the b-scans are out of line because of the delay caused by the time taken for the feedback loop.

In step S150, the offsets determined by the fundus tracking module 810 and received by the OCT beam control unit 800 are collected and two sets of correlated data are calculated. These are:
    offsets produces by the fundus tracking system; and
    a b-scan index or "feedback list" for b-scans associated with these offsets.

The feedback list is sent to the fundus rescan module 820. Here, an algorithm is used to determine the amount of time (or the number of b-scans) passed between the actual misalignment (see ID=5 on FIG. 4) and the OCT b-scan on which the calculated offsets have actually been applied (see ID=9 on FIG. 4). This procedure produces a list of b-scans that are affected by the delay of the feedback loop 600.

The fundus rescan module 820 determines whether b-scans need to be re-scanned. If it finds that there are areas for which the fundus tracking module 810 flagged a fail, such as large eye movement or a blink, it will instruct the OCT beam control unit 800 to rescan the failed b-scans. The fundus rescan module will also determine whether a limit for b-scan repetition has been reached and will not instruct rescans if so. Further to the fundus tracking offset information from the OCT beam control unit 800, the fundus tracking module 810 also receives return information from the OCT beam control unit which describes the b-scan number from the OCT b-scan set on particular offsets are applied.

Before the rescan of the b-scans occurs, there is one more condition. The OCT beam control unit 800 waits for information from the fundus tracking module 810 indicating whether the fundus tracking module can assign offsets (i.e. an "is correct" flag is set to true). The OCT beam controller continues to wait with a timeout for this flag, adding to the potential feedback delay.

In step S160, the fundus rescan module finally instructs the OCT beam control unit to rescan appropriate b-scans in step S170 as determined. The process from step S130 to S160 repeats for the re-scanned b-scans, which may be re-re-scanned according to the same process described above if necessary.

The above process corrects for misalignments in the x-y plane. Misalignments in the z-direction are performed offline.

Smaller z-direction misalignments are possible if the re-scan of the misaligned b-scans is performed immediately after the determination is complete by the fundus rescan module of which b-scans are allocated for re-scanning. However, as this is likely to interrupt the OCT scanning of the full fundus area; and if a specific area suffers from artifacts or the patient being examined is unsteady, a same area may be re-scanned several times before the full OCT image is complete, potentially increasing the time taken to scan the full fundus area or even preventing the whole area from being scanned if the rescan maximum is reached before the whole area is scanned. Thus, a second embodiment performs the re-scans at the end of the respective fundus region examination to ensure a "full capture".

According to another embodiment, there is performed a "multipoint synchronisation" of the scans performed by both the fundus imaging apparatus (such as the SLO) and the OCT. This could be advantageous where the acquisition timing of the OCT and/or SLO is not as reliable, meaning that the "common start" is not necessarily enough to give a reliable b-scan index "feedback list". In this embodiment, after a first common start, if there are variable time intervals between image scans, the b-scans and fundus image scans can desynchronise. Thus, the examination is divided into multiple portions and each portion has a common start process to obtain regular synchronisation points.

Aspects of the present invention can also be realised by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable non-transitory storage medium). A processing apparatus may comprise all of the modules of FIG. 8, or it may comprise the means for the modules to communicate, or any configuration in between. Specifically, a processing apparatus may be supplied separately from the OCT and the SLO devices or it may be a part of the, depending on the configuration of the OCT and SLO devices themselves. Such possible configurations would be understood by the person skilled in the art.

What is claimed is:

1. A method comprising:
   imaging a fundus of an eye to obtain a plurality of fundus images;
   imaging the fundus to obtain a plurality of tomographic images;
   determining a fundus movement of the eyes based on the plurality of fundus image;
   tracking the determined fundus movement of the fundus;
   determining the number and positions of tomographic images imaged during a time including a time during which the fundus movement cannot be tracked;
   re-imaging the determined number of tomographic images at the determined positions.

2. A method according to claim 1, wherein the imaging of the fundus to obtain a fundus image and the imaging of the fundus to obtain a tomographic image have synchronised starts.

3. A method according to claim 1, wherein the time during which the fundus movement cannot be tracked includes the amount of time required to determine whether there is a misalignment in a tomographic image.

4. A method according to claim 1, wherein the time during which the fundus movement cannot be tracked includes a feedback delay for the tracking.

5. A method according to claim 1, wherein the step of determining the fundus movement comprises comparing two fundus images.

6. A method according to claim 1, further comprising replacing the tomographic image imaged in the interval with the re-imaged tomographic images.

7. A method according to claim 1, further comprising outputting a fail flag if the fundus movement cannot be tracked.

8. A method according to claim 1, wherein the fundus image is a 2-dimensional image.

9. A method according to claim 1, wherein the fundus image is an SLO (scanning laser ophthalmoscope) image.

10. A method according to claim 1, wherein the tomographic images are b-scans of an OCT apparatus.

11. An OCT apparatus for use with a processing apparatus, the OCT apparatus comprising:
    an imaging unit operable to image a fundus of an eye to obtain a plurality of tomographic images;
    a communication unit for receiving a number and positions of tomographic images that were imaged during a time period including a time during which the fundus movement cannot be tracked based on a plurality of the fundus images by the processing apparatus; and
    a processor for re-imaging the tomographic images corresponding to the number and the positions of tomographic images received by the communication unit and for replacing the tomographic images that were imaged during the time including the time during which the fundus movement cannot be tracked based on the plurality images by the processing apparatus.

12. An OCT apparatus according to claim 11, further comprising:
    a synchronisation unit for synchronising the start of the imaging of a tomographic image within a region of the fundus by the imaging unit with a start of imaging the same region of the fundus by a fundus imaging apparatus.

13. An OCT apparatus according to claim 11, further comprising:
    a correction unit for correcting a tomographic image position according to the offset received from the processing apparatus.

14. A system for correcting for eye movement during imaging of the eye comprising:
    a processing apparatus comprising:
    an offset measuring unit operable to compare the alignment of a tomographic image imaged by the OCT apparatus with a fundus of an eye to be examined by determining an alignment of the tomographic image compared to a fundus image imaged by the fundus imaging apparatus and by measuring an offset between the fundus image position and a reference fundus position;
    a correction unit operable to correct the position of a subsequently imaged tomographic image based on the offset measured by the offset measuring unit;
    a calculating unit operable to calculate the number of tomographic images that were imaged while the offset measuring unit was measuring the offset; and a communication unit for transmitting to the OCT apparatus the number of tomographic images calculated by the calculating unit;

an OCT apparatus comprising:

an imaging unit operable to image a fundus of an eye to obtain a plurality of tomographic images;

a communication unit for receiving a number of tomographic images that were imaged while the processing apparatus calculated an offset of a tomographic image position with respect to the fundus; and a processor for re-imaging the tomographic images corresponding to the number of tomographic images received by the communication unit and replacing the tomographic images that were imaged while the processing apparatus calculated an offset of a tomographic image position with respect to the fundus with the re-imaged tomographic images; and a fundus imaging apparatus comprising: an imaging unit for imaging a fundus of an eye to obtain a fundus image; and a synchronisation unit for synchronising the start of the imaging of a region of the fundus by the imaging unit with a start of imaging of a tomographic image within the same region of the fundus by an OCT apparatus.

15. A system according to claim 14, further comprising a synchronisation controller for controlling a synchronisation of the imaging of the fundus by the fundus imaging apparatus and the imaging of the tomographic image by the OCT apparatus.

16. A non-transitory storage medium containing a computer program which, when run on a computer, causes the computer to perform the following steps:

imaging a fundus of an eye to obtain a plurality of fundus image;

imaging the fundus to obtain a plurality of tomographic images;

determining a fundus movement of the eye based the plurality of fundus images, and, determining the number and positions of tomographic images imaged in an interval including a time during which the fundus movement cannot be tracked; and re-imaging the determined number of tomographic images at the determined positions.

* * * * *